Figure 1:
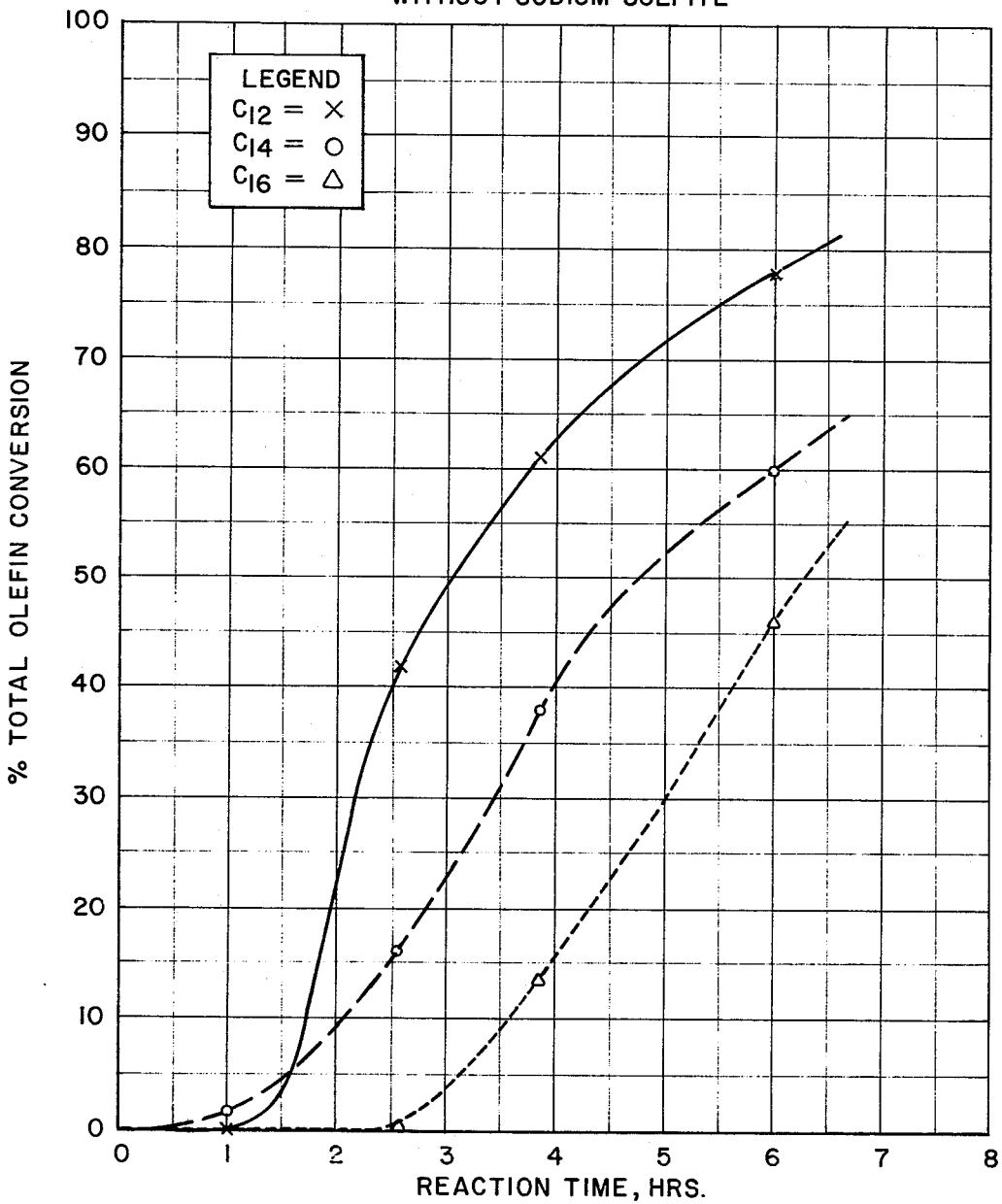

United States Patent [19]

Convers et al.

[11] 4,070,396
[45] Jan. 24, 1978

[54] SULFITE ION CATALYSIS OF BISULFITE ADDITION TO HIGHER MOLECULAR WEIGHT DETERGENT RANGE OLEFINS

[75] Inventors: Ronald J. Convers; Kang Yang, both of Ponca City, Okla.

[73] Assignee: Continental Oil Company, Ponca City, Okla.

[21] Appl. No.: 667,000

[22] Filed: Mar. 15, 1976

[51] Int. Cl.² .................................... C07C 139/12
[52] U.S. Cl. ........................................ 260/513 B
[58] Field of Search ............................ 260/513 B

[56] References Cited

U.S. PATENT DOCUMENTS

| | | | |
|---|---|---|---|
| 2,653,970 | 9/1953 | Fessler | 260/513 B |
| 3,306,931 | 2/1967 | Adams et al. | 260/513 B |
| 3,356,717 | 12/1967 | Furrow | 260/513 B |
| 3,541,140 | 11/1970 | Murphy et al. | 260/513 B |
| 3,579,546 | 5/1971 | Norton | 260/400 |
| 3,706,791 | 12/1972 | Robinette | 260/513 B |
| 3,943,174 | 3/1976 | Ellis et al. | 260/513 B |

*Primary Examiner*—James O. Thomas, Jr.
*Assistant Examiner*—James H. Reamer
*Attorney, Agent, or Firm*—Cortlan R. Schupbach, Jr.

[57] ABSTRACT

Reaction rate and olefin conversion in an organic peroxide initiated addition of water soluble bisulfite to olefins having 12 or more carbon atoms can be increased with the addition of a small amount of water soluble sulfite in combination with an organic solvent and agitation. The catalytic effect of the added sulfite in this reaction system unexpectedly increases as the olefin molecular weight increases, thus allowing convenient and economical sulfitation of mixtures in the $C_{12}$ to $C_{22}$ olefin range.

7 Claims, 3 Drawing Figures

SULFITE ION CATALYSIS OF BISULFITE ADDITION TO HIGHER MOLECULAR WEIGHT DETERGENT RANGE OLEFINS

This invention is directed to a method for increasing the reaction rate of higher molecular weight olefins in the formation of alkanesulfonates. More particularly, this invention is directed to a method of increasing the reaction rate of higher molecular weight internal and pendant olefins to form alkanesulfonates.

The peroxide initiated bisulfite addition of olefins to form sulfonates has long been known. Examples of such processes are those as taught, for example, in U.S. Pat. Nos. 3,168,555; 3,356,717; 3,349,122; 3,479,397; 2,504,411; and German Pat. No. 1,468,023. All relate to the above-mentioned reaction and state that this reaction is effective for olefins.

However, it has long been known that alpha olefins will react much faster and more completely than olefins with pendant or internal unsaturation. Therefore, such less reactive olefins have been regarded as a nuisance and a by-product in the above-mentioned reaction. The alkanesulfonates produced from internal and pendant olefins are effective as detergents, much as those produced from alpha olefins only. However, because of the low reaction rate, these olefins have not heretofore been commercially feasible as a source of alkanesulfonates. In addition, increasing the molecular weight by increasing the chain length rapidly decreases the reaction rate of alpha olefins and especially pendant and internal olefins. Such observations have been made in I&EC Product Research and Development, Volume III, No. 1, March, 1964, page 3. Others can be found in the Journal of Organic Chemistry, Volume 33, 4158 (1968), U.S. Pat. No. 2,318,036, and Chemical Reviews, Volume 27, page 351, by Mayo and Walling. The latter article by Mayo and Walling shows on page 395 that the more hindered olefins are less reactive. It is therefore clear that a process which would allow a reaction rate with pendant and internal olefins comparable to that presently obtained with alpha olefins would be of great benefit.

It is therefore an object of the present invention to provide a method whereby pendant and internal high molecular weight olefins, those having 12 or more carbon atoms, can be increased in reaction rate to form alkanesulfonates. Other objects will become apparent to those skilled in this art as the description proceeds.

It has now been unexpectedly discovered that these less reactive olefins can be made to react at commercially acceptable rates. A method for increasing the reaction rate of $C_{12}$ and higher pendant and internal olefins with bisulfite to form alkanesulfonates, wherein the reaction proceeds by means of a free radical initiator has been devised, the method comprising carrying out the reaction a) in the presence of from about 10 to about 30 mole percent of sulfite ion based on the moles of olefin present b) while in the presence of a solvent system comprising
  1. from about 3 to 6 molar bisulfite in water together with
  2. a mixture of the bisulfite solution described in (1) with an organic solvent selected from the group consisting of 1-propanol and 2-propanol in a volume ratio of from about 1:1 to about 1:3, respectively
  c. at a temperature of from about 60° to about 130° C
  d. while carrying out the reaction under high agitation.

A surprising feature of the instant invention lies in the fact that prior art teachings have considered the use of an organic co-solvent as optional and not necessary or even not preferred (German Pat. No. 1,468,023). In addition, the art has long been aware that pendant and internal olefins, and even alpha olefins of higher molecular weight, have much slower reaction rates than the shorter chain length alpha olefins. The rate increase which can be obtained with the process of the present invention unexpectedly increases as the molecular weight of the olefins goes up. Thus it can be seen that the present process provides a dramatic benefit over the prior art.

The reaction disclosed herein is catalyzed by a small amount of sulfite ion ranging from about 5 to about 40 mole percent based on the total moles of olefins in the reaction. However, best olefin conversions and reaction rates are obtained from about 10 to about 30 mole percent, and optimum or peak results can be found from about 10 to about 20 mole percent. The source of the sulfite ion is not critical other than that any other ions present be inert with respect to the reaction. However, from a standpoint of practicability, sodium sulfite is the preferred sulfite ion source. Other sources such as potassium sulfite can also be used.

The reaction is carried out in the presence of a solvent system which comprises from about 3 to 6 molar bisulfite in water together with a mixture of from about 1:1 to 1:3, respectively, of the bisulfite solution together with an organic solvent. The reaction rate is very sensitive to the type of organic solvent. The organic solvent of this invention is either 1-propanol or 2-propanol.

Bisulfite to olefin mole ratios can vary greatly, but optimum results are normally reached when such ratios range from about 1.0 to 0.9, respectively, to about 2.9 to 0.9, respectively. Preferred ranges are from about 1.9 to 0.9 to about 2.4 to 0.9, respectively. At least 1.0 to 0.9 mole ratios of bisulfite to olefin is necessary.

The reaction is normally carried out at a temperature of from 60° to 130° C. The upper reaction limit is that at which some deterioration of the alkanesulfonate is found. However, a temperature of from 60° to 100° C is preferred, and a range of from 75° to 90° C is most preferred. Pressures range from ambient to superatmospheric although it has been found that ambient pressures give perfectly satisfactory results.

The free radical initiator used is not critical other than the requirement that it generate free radicals at a temperature at or below 130° C. Normally peroxide initiators will be used although initiators such as azobis isobutyronitrile (AIBN) can also be used. Examples of such peroxy initiators are:
tertiary butyl peroxypivalate,
diisobutyryl peroxide,
tertiary butyl perbenzoate,
di (secondary butyl) peroxydicarbonate,
lauryl peroxide, and
methyl ethyl ketone hydroperoxide.

The reaction must necessarily be carried out in the presence of a very high shear agitation in order to bring the water and organic phases into intimate contact. The shear must normally be sufficient to produce a fine emulsion. A micelle mixture, a clear dispersion of both phases, is preferred.

When determining the amount of sulfite ion based on the mole percent of olefin, any standard test to determine the moles of unsaturation in a given weight olefin sample can be used. Examples of such tests are bromine number, nuclear magnetic resonance tests to determine the unsaturation versus the paraffin peaks, and hydrogen uptake. All these tests are well known to those skilled in this art.

It has been known for some time that higher molecular weight olefins react with bisulfite under free radical conditions more slowly than their lower molecular weight homologs. The differences in reaction rates can cause the use of higher molecular weight detergent range olefins, pendant and internal olefins, or their mixtures, to be both uneconomical and inconvenient because of longer required reaction times and/or special recycling of unreacted olefins. In the process of the instant invention, ideal conditions would include a small recycle of the product alkanesulfonates for use as a surfactant in order to make the shear less critical in carrying out the reaction. However, the reaction can be carried out quite satisfactorily under high shear conditions without the use of surfactants or introduction of a minor amount of product into the reaction.

According to the present invention, a small amount of water soluble sulfite, particularly sodium sulfite, increases the rate of olefin conversion in the organic peroxide initiated addition of water-soluble bisulfite to olefins having 12 or more carbon atoms. As explained above, the effect unexpectedly increases with increases in molecular weight of the olefin thus allowing more convenient and economical sulfitation of mixtures of detergent range ($C_{12}$ and higher) olefins. The effect is primarily confined to pendant and internal olefins. The effect appears to optimize as the sodium sulfite/olefin mole ratio approaches zero while sodium bisulfite concentration increases. It is clear from the prior art that higher sodium bisulfite concentrations in and of themselves result in greater reaction rates and conversions among alpha olefins. However, this effect has not heretofore been reported with respect to the pendant and internal olefins.

The invention is more concretely described with reference to the examples and figures below wherein all parts and percentages are by weight unless otherwise stated. The examples are intended to exemplify the present invention and should not be construed to limit it.

The following reactions were carried out under nitrogen atmosphere in a 500 milliliter (ml) flask equipped with constant high speed stirring. About 0.5 ml per hour constant feed of a 75 percent mineral oil solution of tertiary butyl peroxypivalate was added as a free radical initiator, followed by heating to temperatures which caused rapid decomposition of said initiator. The olefin conversions were monitored by gas liquid chromatography (glc). Conversion figures were obtained during the reaction by comparison with the ratios of olefins and paraffins in the starting samples. Final conversion figures were obtained using internal glc standards added at the end of the reaction.

EXAMPLE 1

A mixture of $C_{12}$, $C_{14}$, and $C_{16}$ pendant olefins (19 grams, 0.09 moles), 21 grams of sodium bisulfite, 40 ml of distilled water, and 40 ml of 2-propanol were stirred at about 3,000 rpm at about 79° C with a constant initiator feed over 6 hours. The olefins (dimers of low molecular weight alpha olefins) had glc peak areas of 12.8 percent, 25.6 percent, and 4.6 percent, respectively. The mixture contained about 11 mole percent internal olefins and about 9 glc peak area percent paraffins. The olefin conversion data were plotted and are shown in FIG. 1. It can be seen from an analysis of FIG. 1 that the lower molecular weight olefins reacted at a much faster rate than the higher molecular weight olefins.

EXAMPLE 2

Figure 2:
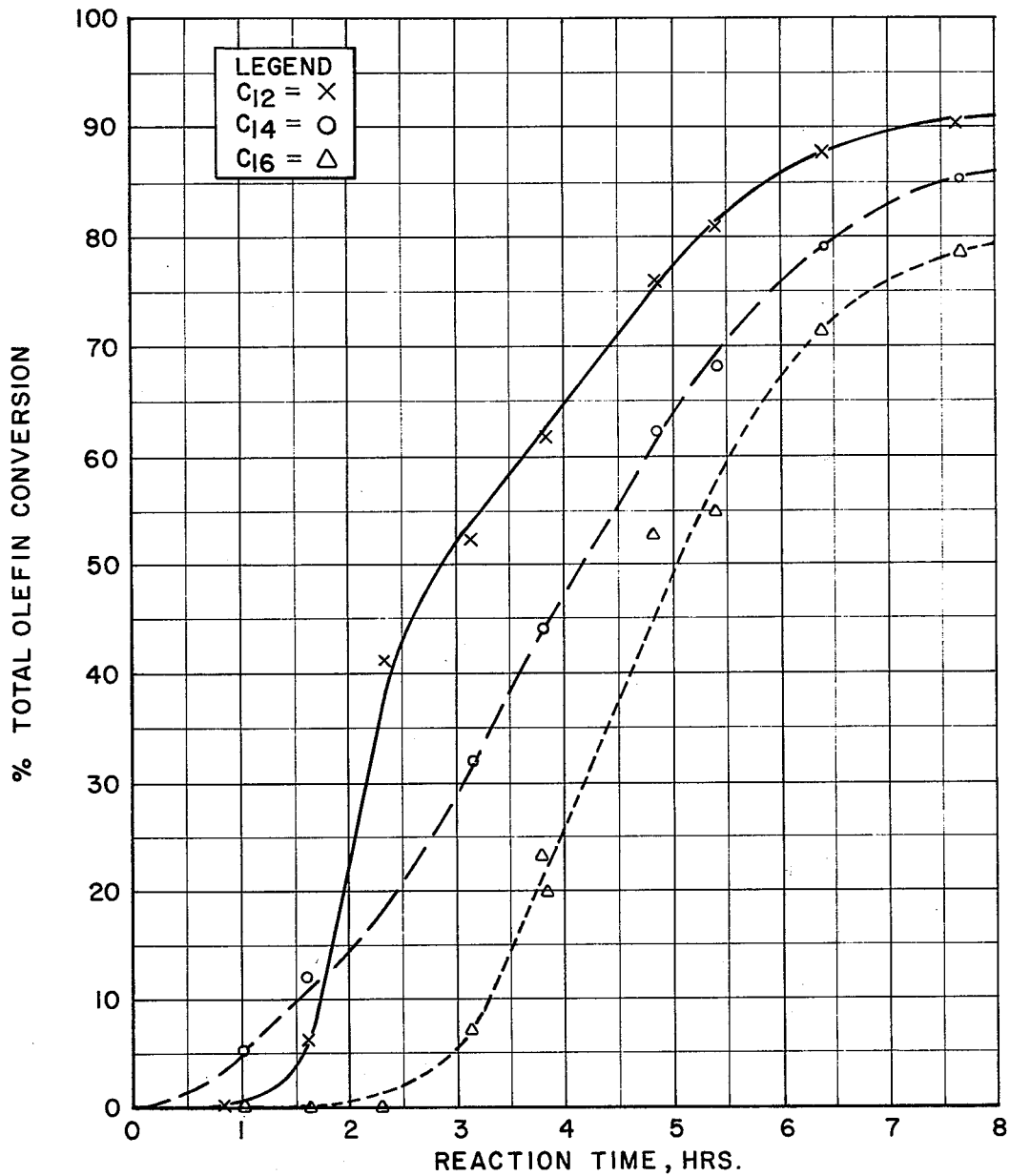

A mixture of pendant olefins as described in Example 1 (19 grams), 20 grams of sodium bisulfite, 1.3 grams of sodium sulfite, 40 ml of distilled water, and 40 ml of 2-propanol were stirred at about 3,000 rpm at about 79° C with constant initiator feed over a 7-hour, 39-minute period. The olefin conversion data were determined and plotted as shown in FIG. 2. An analysis of FIG. 2 shows the increased reaction rate of the higher molecular weight pendant and internal olefins when compared to the FIG. 1 plot. The reaction benefits are clear and distinct. A comparison of the 6-hour data, for example, shows that the $C_{16}$ pendant olefin conversion went from 46% to 67%.

EXAMPLE 3

A mixture of 22.4 grams of 2-hexyl-1-decene containing about 10.5 mole percent of an internal $C_{16}$ olefin and about 9 glc peak area percent of a $C_{16}$ paraffin together with 20 grams of sodium bisulfite, 40 ml of distilled water, and 40 ml of 1-propanol were stirred at about 2,000 rpm at about 87° C with constant 0.5 ml/hr feed of 34% t-butyl peroxypivalate in mineral spirits over a 5-hour period to afford a total olefin conversion of 42.6 percent.

EXAMPLE 4

The reaction was carried out in an identical manner with that of Example 3 except that 0.6 grams of sodium sulfite were added in the beginning. Total olefin conversion after 5 hours was 43.4 percent.

EXAMPLE 5

The reaction was carried out in an identical manner with Example 3 except that 1.3 grams of sodium sulfite was added in the beginning. Total olefin conversion after 5 hours was 52 percent.

EXAMPLE 6

The reaction was carried out in an identical manner with that of Example 3 except that 3 grams of sodium sulfite was added in the beginning. Total olefin conversion after 5 hours was 48.6 percent.

EXAMPLE 7

Figure 3:
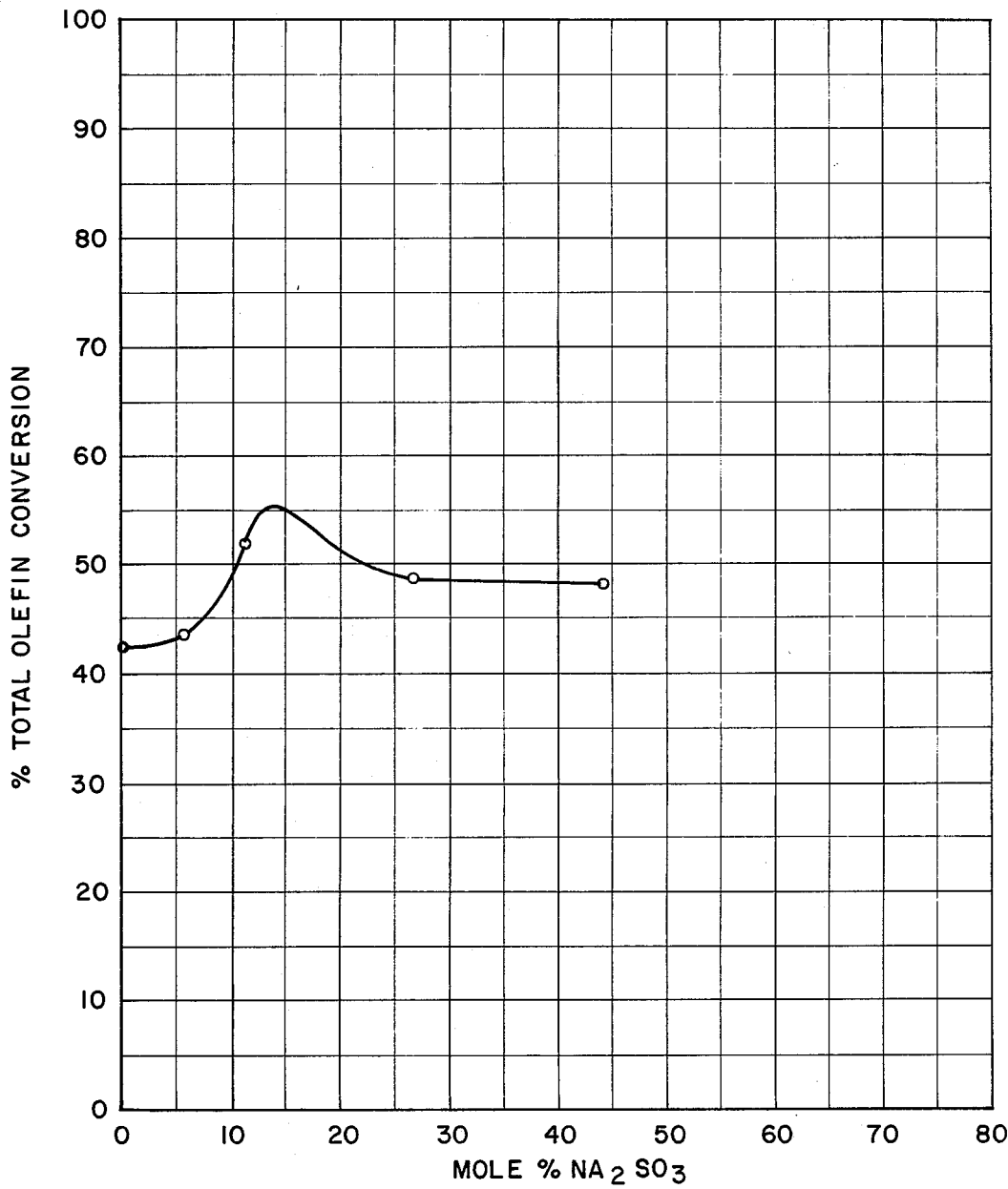

The reaction was carried out in an identical manner with that of Example 3 except that 5 grams of sodium sulfite were added in the beginning. Total olefin conversion after 5 hours was 48.1 percent. The results of Examples 3 through 7 have been plotted and are shown as FIG. 3. It can be seen that the effect of sulfite addition has an optimum and thereafter gradually decreases with increased sodium sulfite.

The effects of organic solvent type, bisulfite concentration, and the use of olefin mixtures were tested by carrying out peroxide initiated addition of sodium bisulfite to $C_{12}$ and $C_{16}$ pendant olefins. The reactions involved were run in pairs in 500 ml flasks with 2,000 rpm constant stirring under nitrogen and a constant feed of t-butyl peroxypivalate in mineral spirits at about 0.5 ml/hr from a double syringe pump. The paired reactions were run with differing variables so as to yield simultaneous conversion data staggered about any possible optimum. Pendant olefins used contained about 11 mole percent internal olefins and about 9 glc peak area percent paraffins. The results are shown in Tables I, II, and III, respectively.

Table IV shows the effect of sodium sulfite concentration. The initiator used was t-butyl peroxypivalate in mineral spirits fed continuously at about 0.5 ml/hr. Tests 10 through 13 were carried out using a sodium bisulfite different from that used in Tests 1 through 9.

TaBLE I
EFFECT OF SOLVENT

| Olefin (Moles) | NaHSO$_3$ Moles | Na$_2$SO$_3$ Moles | Solvent (ml) | H$_2$O ml | Time Hours | Temp. °C. | Total Olefin Conversion, % |
|---|---|---|---|---|---|---|---|
| C$_{16}$(0.09) | 0.19 | 0.010 | 2-C$_3$H$_7$OH(40) | 40 | 6.2 | 79 | 31[a] |
| C$_{16}$(0.09) | 0.19 | 0.010 | 1-C$_3$H$_7$OH(40) | 40 6.2 | 79 | 66[a] | |
| C$_{16}$(0.09) | 0.19 | 0.010 | DMF(80)[c] | 0 | 5.0 | 80 | 0[b] |
| C$_{16}$(0.09) | 0.19 | 0.010 | DMF(40)[c] | 40 | 4.0 | 80 | 0[b] |
| C$_{16}$(0.09) | 0.19 | 0.010 | HOAc(80)[d] | 0 | 5.25 | 80 | 10[b] |

[a]Initiator: ca. 75% active peroxide.
[b]Initiator: 89% active peroxide.
[c]DMF = dimethylformamide
[d]HOAc = glacial acetic acid

TABLE II
EFFECT ON NaHSO$_3$ CONCENTRATION

| Olefin (Moles) | NaHSO$_3$ Moles | Na$_2$SO$_3$ Moles | 1-C$_3$H$_7$OH ml | H$_2$O ml | Time Hours | Temp. °C. | Total Olefin Conversion, % |
|---|---|---|---|---|---|---|---|
| C$_{12}$(0.09) | 0.19 | 0.010 | 40 | 40 | 6.0 | 87 | 91[a] |
| C$_{12}$(0.09) | 0.10 | 0.010 | 40 | 40 | 6.0 | 87 | 65[a] |
| C$_{16}$(0.09) | 0.10 | 0.010 | 40 | 40 | 5.0 | 87 | 20[a] |
| C$_{16}$(0.09) | 0.19 | 0.010 | 40 | 40 | 5.0 | 87 | 39[b] |
| C$_{16}$(0.09) | 0.19 | 0.010 | 40 | 40 | 5.0 | 87 | 37[b] |
| C$_{16}$(0.09) | 0.24 | 0.010 | 40 | 40 | 5.0 | 87 | 45[b] |
| C$_{16}$(0.09) | 0.19 | 0.010 | 40 | 40 | 5.0 | 87 | 43[b] |
| C$_{16}$(0.09) | 0.29 | 0.010 | 40 | 40 | 5.0 | 87 | 37[b] |
| C$_{12}$(0.09) | 0.10 | 0.010 | 40 | 40 | 4.0 | 87 | 73[c] |
| C$_{12}$(0.09) | 0.10 | 0.010 | 40 | 20 | 4.0 | 87 | 87[c] |
| C$_{12}$(0.09) | 0.10 | 0.010 | 40 | 30 | 4.0 | 87 | 79[c] |
| C$_{12}$(0.09) | 0.10 | 0.010 | 40 | 15 | 4.0 | 87 | 84[c] |
| C$_{12}$(0.09) | 0.10 | 0.010 | 40 | 25 | 4.0 | 87 | 83[c] |
| C$_{12}$(0.09) | 0.10 | 0.010 | 40 | 10 | 4.0 | 87 | 54[c] |

[a]Initiator: ca. 75% active peroxide.
[b]Initiator: 34% active peroxide.
[c]Initiator: 87% active peroxide.

TABLE III
EFFECT OF OLEFIN MIXTURE ON CONVERSION RATE OF HIGHER MW PENDANT OLEFIN

| Olefin (Moles) | NaHSO$_3$ Moles | Na$_2$SO$_3$ Moles | 1-C$_3$H$_7$OH ml | H$_2$O ml | Time Hours | Temp. °C. | Total Olefin Conversion, % |
|---|---|---|---|---|---|---|---|
| C$_{12}$(0.045) | 0.24 | 0.010 | 40 | 40 | 6.7 | 87 | 78[a] |
| C$_{16}$(0.045) | | | | | | | 56 |
| C$_{16}$(0.09) | 0.24 | 0.010 | 40 | 40 | 6.7 | 87 | 50[a] |

[a]Initiator: 34% active peroxide.

TABLE IV
EFFECT OF Na$_2$SO$_3$ CONCENTRATION

| Test | C$_{16}$ Olefin Moles | NaHSO$_3$ Moles | Na$_2$SO$_3$ Moles | 1-C$_3$H$_7$OH ml | H$_2$O ml | Time Hours | Temp. °C. | Total Olefin Conversion, % |
|---|---|---|---|---|---|---|---|---|
| 1 | 0.09 | 0.10 | — | 40 | 40 | 5.0 | 87 | 17[a] |
| 2 | 0.09 | 0.10 | 0.010 | 40 | 40 | 5.0 | 87 | 20[a] |
| 3 | 0.09 | 0.10 | 0.10 | 40 | 40 | 5.0 | 87 | 25[a] |
| 4 | 0.09 | 0.19 | — | 40 | 40 | 5.0 | 87 | 43[a] |
| 5 | 0.09 | 0.19 | 0.005 | 40 | 40 | 5.0 | 87 | 43[a] |
| 6 | 0.09 | 0.19 | 0.010 | 40 | 40 | 5.0 | 87 | 52[a] |
| 7 | 0.09 | 0.19 | 0.040 | 40 | 40 | 5.0 | 87 | 48[a] |
| 8 | 0.09 | 0.19 | — | 40 | 40 | 5.0 | 87 | 39[b] |
| 9 | 0.09 | 0.19 | 0.024 | 40 | 40 | 5.0 | 87 | 49[b] |
| 10 | 0.09 | 0.19 | 0.010 | 40 | 40 | 5.0 | 87 | 37[b] |
| 11 | 0.09 | 0.24 | — | 40 | 40 | 5.0 | 87 | 42[b] |
| 12 | 0.09 | 0.24 | 0.010 | 40 | 40 | 5.0 | 87 | 45[b] |
| 13 | 0.09 | 0.24 | 0.024 | 40 | 40 | 5.0 | 87 | 40[b] |

[a]Initiator: ca. 75% active peroxide.
[b]Initiator: 34% active peroxide.

EXAMPLE 8

In a similar set of experiments, 0.09 moles of 2-hexyl-1-decene, 0.24 moles of sodium bisulfite, 0.01 moles of sodium sulfite, 40 ml of water, and 40 ml of n-propanol were reacted in a 300 ml stainless steel autoclave. The reaction temperatures were selected to provide roughly equal radical populations during the reaction time. The initiator was fed continuously. The results are shown in Table V on the following page.

TABLE V
TEMPERATURE EFFECTS ON THE BISULFITE-PENDANT OLEFIN REACTION

| Run No. | Time Hrs. | Temp. (° C) | Initiator | Feed Rate ml/hr | % Total Olefin Conversion |
|---|---|---|---|---|---|
| 87 | 5.0 | 85–8 | A | 0.5 | 33 |
| 89[a] | 5.0 | 87–92 | A | 0.5 | 42 |
| 90 | 5.0 | 104–6 | B | 0.75 | 27 |
| 91 | 5.0 | 112–8 | B | 0.75 | 11 |
| 92 | 5.0 | 140–3 | C | 0.5 | 0 |
| 93 | 5.0 | 147–53 | C | 0.5 | 28[b] |

A 87% t-butyl peroxypivalate in mineral spirits.
B 54% t-butyl peroxyoctoate in mineral spirits.
C ca. 75% t-butyl peroxyacetate in mineral spirits.
[a]The reactor's interior was spray coated with Teflon.
[b]Glc data showed numerous $C_{16}$ compounds and increased $C_{16}$ internal olefin content in the unreacted olefin.

mineral spirits. In runs D and E, the initiator was a solution of 32.1 ml of 5.25% aqueous NaOCl and 1.71 g of 50% aqueous NaOH. In run B the initiator feed was slightly restricted during the last two hours of the run, and somewhat higher yields would be anticipated under normal reaction conditions. The surfactant in all cases was a deoiled sample of mixed $C_{12}$, $C_{14}$, $C_{16}$ pendant alkanesulfonates.

TABLE VI
REACTION CONDITIONS

| Run | Olefin (Moles) | NaHSO$_3$ (Moles) | Na$_2$SO$_3$ (Moles) | H$_2$O (ml) | n-PrOH (ml) | Initiator (Feed Rate) | Surfactant (grams) |
|---|---|---|---|---|---|---|---|
| A | C$_{16}$ Pendant 0.090 | 0.19 | 0.016 | 70 | 0 | Peroxide (ca 0.5 ml/hr) | 30 |
| B | C$_{16}$ Pendant 0.045 | 0.15 | 0.010 | 40 | 40 | Peroxide (ca 0.5 ml/hr) | 15 |
| C | C$_{16}$ Internal[a] 0.045 | 0.15 | 0.010 | 40 | 40 | Peroxide (ca 0.5 ml/hr) | 15 |
| D | C$_{16}$ Pendant 0.045 | 0.15 | 0.010 | 40 | 40 | NaOCl (ca 2.8 ml/hr) | 15 |
| E | C$_{14}$ Internal[b] 0.045 | 0.15 | 0.010 | 40 | 40 | NaOCl (ca 2.8 ml/hr) | 15 |

[a]Containing 10% n-$C_{14}H_{30}$
[b]Containing 10% n-$C_{12}H_{26}$

TABLE VII
PERCENT OLEFIN CONVERSIONS

| Reaction Time, Hrs. | A | B | C | D | E |
|---|---|---|---|---|---|
| 1 | 0 | 30 | 19 | 7 | — |
| 2 | 0.2 | 51 | 29 | 11 | — |
| 3 | 0.9 | 61 | 36 | 15 | — |
| 4 | <2 | 70 | 43 | 18 | 16 |

Runs A and B in Tables VI and VII show that an organic co-solvent (propanol) is necessary for useful high molecular weight pendant olefin conversion. The data are also applicable to the even more slowly reacting detergent range internal olefins. Table VIII, together with Tables VI and VII, show that the practical limits of the useful alcohol/H$_2$O volume ratio are about 1:2 to 4:1 respectively. The optimum alcohol/H$_2$O volume ratio seems to be about 2:1.

TABLE VIII
EFFECT OF ALCOHOL VOLUME CHANGE[a]

| Run | Olefin (Moles) | NaHSO$_3$ Moles | Na$_2$SO$_3$ Moles | H$_2$O ml | 1-C$_3$H$_7$OH ml | Temp. ° C. | Time Hours | Total Olefin Conversion, % |
|---|---|---|---|---|---|---|---|---|
| A | C$_{12}$(0.09) | 0.10 | 0.01 | 20 | 60 | 87 | 3.2 | 88 |
| B | C$_{12}$(0.09) | 0.10 | 0.01 | 20 | 20 | 87 | 3.2 | 87 |
| C | C$_{12}$(0.09) | 0.10 | 0.010 | 20 | 40 | 87 | 4.0 | 87[a] |

[a]In runs A and B, a total of 2.3 ml of 87% t-butyl peroxypivalate initiator was used. In run C, a total of 2.0 ml of the same initiator was used. Thus, the results of A and B are not absolutely comparable to those of C, but the rate differences expected from the different amounts of initiator added suggest that 20 ml of H$_2$O:40 ml of 1-propanol is optimal for the above reaction.

EXAMPLE 9

A series of experiments was carried out to test the performance of German Pat. No. 1,468,023 which teaches aqueous surfactants as a solvent system and prefers sodium hypochlorite initiation in order to prepare sodium alkanesulfonates from terminal or internal olefins. The results summarized in Tables VI and VII show that an alcoholic co-solvent is necessary with pendant olefins even when strong surfactant solutions are used. Glc data also indicate a marked increase in reactivity of internal straight chain aliphatic olefin isomers as the double bond approaches the terminal carbon atom.

The experiments were run as previously described in 500 ml flasks at about 85° C with about 2,000 rpm constant stirring and constant initiator feed. In runs A, B, and C, the initiator was 89% t-butyl peroxypivalate in It will be clear from a review of the above data and the teachings made herein that the unique described combination of conditions allows the useful conversion of higher molecular weight (C$_{12}$ and higher) internal and pendant olefins to valuable alkanesulfonates. Previous rate difficulties associated with differences in olefinic double bond substitution have been overcome. Detergent range pendant and internal olefins, generally very unreactive towards sodium bisulfite, have now been reacted in commercially acceptable rates. Three unexpected catalytic effects of sulfite have been determined under the conditions of the instant invention. First, a general rate enhancement is found for more slowly reacting olefin types (internal and pendant). Secondly, added sulfite shows unexpected olefin conversion optima at low sulfite/olefin mole ratios.

Thirdly, the effect of added sulfite under the conditions herein described unexpectedly increases with increases in olefin molecular weight ($C_{12}$ and higher).

While certain embodiments and details have been shown for the purpose of illustrating this invention, it will be apparent to those skilled in this art that various changes and modifications may be made herein without departing from the spirit or the scope of the invention.

We claim:

1. In the process of reacting $C_{12}$ and higher pendant and internal olefins with bisulfite to form alkanesulfonates wherein the reaction proceeds by means of a free radical initiator, wherein the rate increases as the molecular weight of the said olefin increases, the improvement comprising carrying out the reaction:
    a. in the presence of from about 10 to about 30 mole percent of water soluble sulfite ion based on the moles of olefins present;
    b. in the presence of a solvent system comprising
        1. about 3 to 6 molar water soluble bisulfite in water together with;
        2. a mixture of bisulfite solution of part (1) with an organic solvent selected from the group consisting of 1-propanol and 2-propanol in volume ratios of from 1:1 to about 1:3 respectively wherein the mole ratio of bisulfite to olefin is at least 1.0 to 0.9,
    c. at a temperature of from about 60° to about 130° C;
    d. under agitation.

2. A method as described in claim 1 wherein the reaction is carried out at temperatures of from about 60° to about 100° C.

3. A method as described in claim 1 wherein the agitation is sufficient to produce a fine emulsion.

4. A method as described in claim 1 wherein the agitation is sufficient to produce a micelle solution.

5. A method as described in claim 1 wherein the free radical initiator is tertiary butyl peroxypivalate.

6. A method as described in claim 1 wherein the free radical initiator is azobis-isobutyronitrile.

7. A method as described in claim 1 wherein the reaction is carried out in the presence of added deoiled product surfactant.

* * * * *

UNITED STATES PATENT OFFICE
CERTIFICATE OF CORRECTION

PATENT NO. : 4,070,396
DATED : January 24, 1978
INVENTOR(S) : Ronald J. Convers and Kang Yang It is certified that error appears in the above-identified patent and that said Letters Patent are hereby corrected as shown below:

In Table I of the specification the last four columns should read as follows:

| $H_2O$ ml | Time Hours | Temp °C | Total Olefin Conversion % |
|---|---|---|---|
| 40 | 6.2 | 79 | $31^a$ |
| 40 | 6.2 | 79 | $66^a$ |
| 0 | 5.0 | 80 | $0^b$ |
| 40 | 4.0 | 80 | $0^b$ |
| 0 | 5.25 | 80 | $10^b$ |

Signed and Sealed this

Twentieth Day of June 1978

[SEAL]

Attest:

RUTH C. MASON
Attesting Officer

DONALD W. BANNER
Commissioner of Patents and Trademarks